US00PP24597P3

(12) United States Plant Patent
Korlipara

(10) Patent No.: US PP24,597 P3
(45) Date of Patent: Jul. 1, 2014

(54) *CAREX* PLANT NAME 'SPARK PLUG'

(50) Latin Name: *Carex phyllocephala*
Varietal Denomination: Spark Plug

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 132 days.

(21) Appl. No.: 13/573,509

(22) Filed: Sep. 19, 2012

(65) Prior Publication Data

US 2014/0082788 P1 Mar. 20, 2014

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — Wendy C Haas

(74) *Attorney, Agent, or Firm* — Klarquist Sparkman, LLP

(57) ABSTRACT

A new and distinct *Carex phyllocephala* plant characterized by variegated leaves with a dark center stripes and white to cream margins, small, multi-crowned, low mounding habit, and good vigor.

1 Drawing Sheet

Botanical denomination: *Carex phyllocephala.*
Variety designation: 'Spark Plug'.

BACKGROUND OF THE INVENTION

The present invention relates to a new and distinct cultivar of *Carex phyllocephala* and given the cultivar name of 'Spark Plug'. *Carex phyllocephala* is in the family Cyperaceae. The new cultivar originated from a whole plant tissue culture mutation of *Carex phyllocephala* 'Sparkler'. It is an excellent choice for use in a moist, light shade location in a small garden.

Compared to *Carex phyllocephala* 'Sparkler', the new cultivar is half the height with a more compact habit and shorter, narrower variegated leaves.

The new *Carex phyllocephala* is uniquely distinguished by:

1. variegated leaves with a dark center stripes and white to cream margins,
2. small, multi-crowned, low mounding habit,
3. good vigor.

The new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a one-year-old plant of *Carex phyllocephala* 'Spark Plug' growing in a one gallon pot in a cold greenhouse in April in Canby, Oreg.

FIG. 2 shows a close up of two-year-old plant in flower in the garden in late July in Canby, Oreg.

DETAILED PLANT DESCRIPTION

The following is a detailed description of the new *Carex phyllocephala* cultivar based on observations of three-year-old specimens growing in the garden in late July in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* 1999 edition, 5$^{th}$ edition.

Plant:

*Form.*—Basal rosette, herbaceous perennial with short and slightly thick, ligneous rhizome.
*Hardiness.*—USDA Zones 8 to 12.
*Size.*—32 cm tall from top of the foliage to the ground and 50 cm wide.
*Number of culms.*—50 to 70.
*Habit.*—Clumping, erect.
*Vigor.*—Good.

Culm:

*Description.*—Bamboo-like, rather stout, obtusely trigonous, clothed with reddish brown and bladeless sheaths at lower part.
*Size.*—Grows to 30 cm tall and 4 mm wide.
*Internodes.*—7 cm at the base becoming shorter up the culm, to 7 mm.
*Surface texture.*—Glabrous.
*Color.*—Yellow Green 146A under the sheath, sheath Greyed Purple 187A to Brown 200B.

Leaf:

*Type.*—Simple.
*Arrangement.*—In whorls, clustered toward the top of the culms.
*Shape.*—Linear.

*Venation*.—Parallel.
*Margins*.—Entire.
*Apex*.—Accuminate.
*Base*.—A sheath.
*Blade size*.—Grows to 19 cm long and 12 mm wide.
*Surface texture*.—Glabrous.
*Leaf color*.—Topside, creamy margins and center stripes Yellow 8D, green center stripes Green 137A; bottom side, creamy margins and center stripes Yellow 8D, green stripes Green 138B and 138C.

Inflorescence: Not showy.
*Type*.—Monoecious with the terminal spike male and lateral spikes female.
*Number of spikes*.—1 male, 5 to 6 female.
*Description*.—Linear-cylindric, shortly pedunculate.
*Size*.—Males spike grows to 3 cm long and 2 mm wide, female spikes grow to 3 cm long and 4 mm wide.
*Number of flowers per spike*.—About 150 male and 70 female.
*Peduncle*.—Grows to 7 mm long and less than 1 mm wide, glabrous, Green 138B.
*Bloom period*.—Late July to August in Canby, Oreg.

Flower:
*Type*.—Monoecious, incomplete, with no tepals.
*Female*.—Glumes green at middle, Green 138B, pale laterally, Greyed Yellow 160B, very shortly ferruginous striate, broadly obovate, ca. 1.8 mm, membranous, 3-veined, apex acute, mucronate; style base slightly thickened; stigmas 3.
*Male*.—About 1 mm long, tawny colored, Grey Brown 199B, pollen White 155A.
*Fragrance*.—None.
*Lastingness*.—Each spike lasts for about 4 weeks.

Fruit: A dry, one-seeded achene, not seen.
Pest and disease tolerance: The new cultivar is typical to the genus. No known resistances to pests or diseases. No problems have been found in Canby, Oreg.

I claim:
1. A new and distinct *Carex phyllocephala* plant as herein illustrated and described.

* * * * *

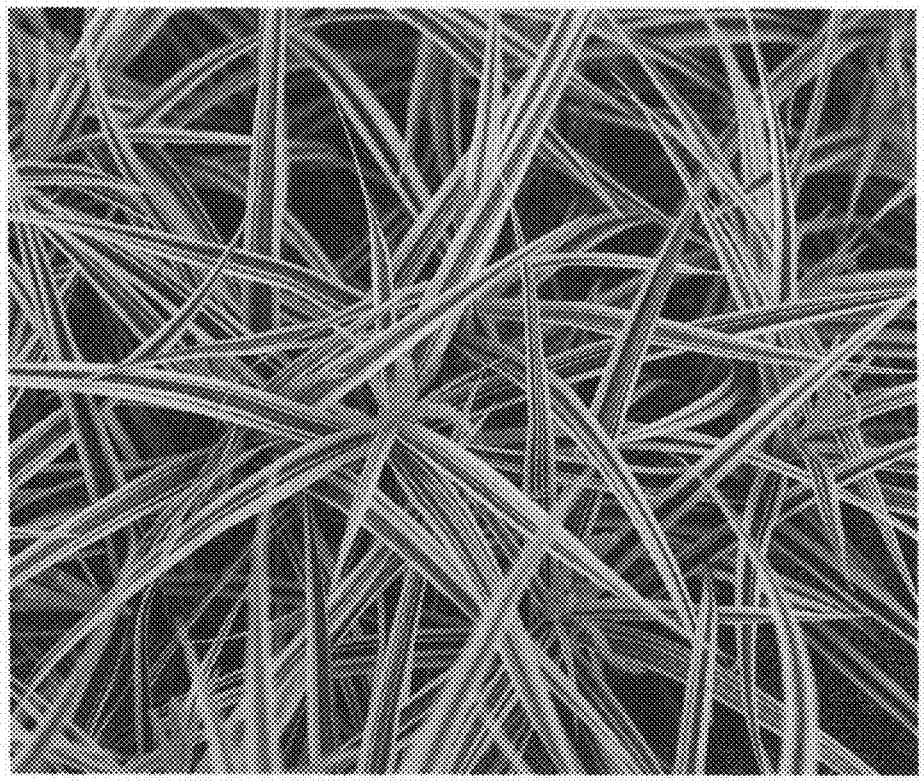

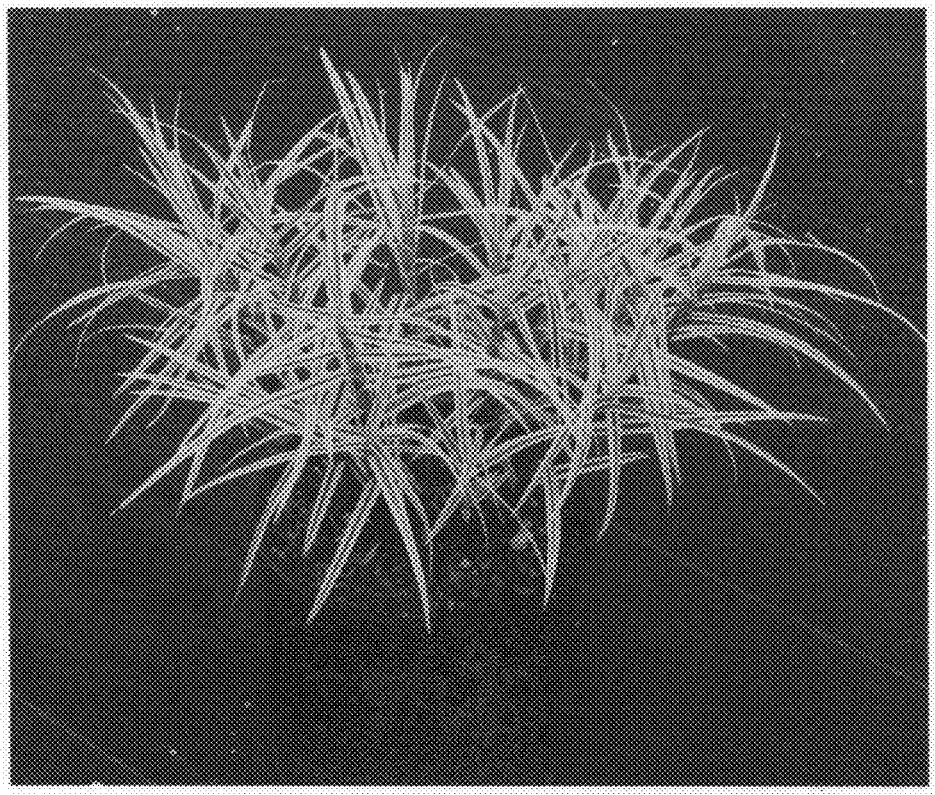
FIG. 1 above, FIG. 2 below